(12) United States Patent
Duschek et al.

(10) Patent No.: US 6,733,820 B1
(45) Date of Patent: May 11, 2004

(54) METHOD FOR DETERMINING DIRECTION-DEPENDENT PROPERTIES OF ENAMELS

(75) Inventors: Wolfgang Duschek, Münster (DE); Bernd Biallas, Albesloh (DE)

(73) Assignee: BASF Coatings AG, Munster (DE)

( * ) Notice: Subject to any disclaimer, the term of this patent is extended or adjusted under 35 U.S.C. 154(b) by 0 days.

(21) Appl. No.: 09/743,049

(22) PCT Filed: Jun. 30, 1999

(86) PCT No.: PCT/EP99/04497

§ 371 (c)(1),
(2), (4) Date: Jan. 17, 2001

(87) PCT Pub. No.: WO00/03212

PCT Pub. Date: Jan. 20, 2000

(30) Foreign Application Priority Data

Jul. 9, 1998 (DE) .......................................... 198 30 745

(51) Int. Cl.$^7$ ................................................. B05D 3/14
(52) U.S. Cl. .......................................... 427/9; 427/421
(58) Field of Search ..................................... 427/9, 421

(56) References Cited

U.S. PATENT DOCUMENTS

| | | | |
|---|---|---|---|
| 5,500,274 A | 3/1996 | Francis et al. | 428/156 |
| 5,597,861 A | 1/1997 | Nakae et al. | 524/601 |
| 5,991,042 A | 11/1999 | Rupieper et al. | |
| 6,459,477 B1 | 10/2002 | Berlin et al. | |

FOREIGN PATENT DOCUMENTS

| | | | | |
|---|---|---|---|---|
| DE | 196 05 520 C1 | 2/1996 | | G01B/11/30 |
| DE | 196 11 062 C1 | 3/1996 | | G01J/3/46 |
| DE | 197 09 406 A1 | 3/1997 | | G05D/21/02 |
| EP | 0 359 891 A1 | 7/1989 | | B05B/13/04 |

OTHER PUBLICATIONS

Abstract for EP 0350891 From EPO, 1990–01–07.

*Primary Examiner*—Bernard Pianalto

(57) ABSTRACT

A method of determining direction-dependent properties of coatings, in which measurements of coating properties are made along a test track (4a, 4b) on a sample coating using one or more measuring instruments and at least one measurement is recorded in relation to direction (6). The course of the sample coating is such that there are points of identical coat thickness (2) with different coat-thickness gradients (5) along the test track.

14 Claims, 1 Drawing Sheet

METHOD FOR DETERMINING DIRECTION-DEPENDENT PROPERTIES OF ENAMELS

The present invention relates to a method of determining direction-dependent properties of coatings, in which measurements of coating properties are made along a test track on a sample coating using one or more measuring instruments.

For the development and quality control of paints and other coating materials it is necessary to investigate the resulting coatings in respect of a variety of properties. To this end, sample coatings are produced for which the designation "test panels" has become established, on account of the fact that the sample-coated article is generally platelike.

The properties investigated with the aid of test panels relate to a broad spectrum of relevant properties of the coating. They include on the one hand the optical properties, especially the color properties of the coating (shade, gloss, evenness, effect properties, haze, hiding power). On the other hand, the mechanical properties are of interest, such as the hardness of the coating, its adhesion to the substrate, and elasticity. Finally of interest are further physical properties, such as the diffusion capacity of foreign substances in the coat, the electrical conductivity of the coat, the UV absorbency, the lame retarding effect, and the resistance of the coat under stresses as encountered in practice.

A variety of methods have been developed for the efficient measurement of the test panels. For instance, DE-196 40 376.6 describes an automated method of measuring coated test panels. In that method a robot guides various measuring instruments along predetermined test tracks over the test panel, and electronically records the measurements obtained. The determination of the coat-thickness dependency of various parameters in a single measuring operation is the aim of DE 196 05 520 C1. For this purpose, a wedge-shaped coating film is applied and both the coat thickness and the optical parameters are measured in each case along a gridlike screen.

However, the methods referred to have the disadvantage that they do not take sufficient account of the directional dependency of the measurements. In the case of effect coatings, for example, as widely used in automotive finishing, however, the angular dependency of optical properties plays an important part. For the measurements to be meaningful it is therefore vital to take into account the angular conditions relative to the coat surface under which said measurements were taken, and to obtain sufficient measurements to allow recognition of functional correlations.

In the case where the coat thickness varies, moreover, it may be important to know the situation of the measurement direction relative to the coat-thickness gradient. This mutual dependency of measurement direction and coat-thickness gradient is not taken into account, and certainly not efficiently recorded, in any of the prior art methods.

In contrast, the present invention has set itself the object of avoiding the disadvantages of the prior art and of providing a method which can be carried out efficiently, simply, and automatically as well if desired, and which in one measurement pass makes it possible to detect direction-dependent measurements and also a dependency of the measurements on the coat-thickness gradient.

This object is achieved by means of a method in which measurements of coating properties are made along a test track on a sample coating using one or more measuring instruments. At least one measurement is to be recorded in relation to direction, i.e., it depends on the relative angle between the measurement direction and a second direction, e.g., the film surface and/or the coat-thickness gradient. This coat-thickness gradient is a two-dimensional parameter (vector) which points in the direction of the steepest increase in coat thickness.

Moreover, the course of the sample coating and of the test track is such that there is at least one coat thickness of the sample coating which occurs at least twice and with different coat-thickness gradients along the test track. Once during the measurement along the test track, in other words, a coat thickness $SD_0$ is traversed where there is a certain coat-thickness gradient $\underline{G}_1$ (increase or decrease in coat thickness), and this coat thickness $SD_0$ is subsequently traversed a second time with a different coat-thickness gradient $\underline{G}_2$.

The method of the invention has the advantage that, in a single measurement pass (measurement along the test track), measurements are made at different angles between measurement direction and coat-thickness gradients $\underline{G}$ for at least one coat thickness $SD_0$. Any mutual dependency of these directions that leads to measurable differences is immediately recognized. This is important, for example, for many optical properties of effect coatings, in the case of which such deviations are not desired.

Preferably, the corresponding coat-thickness gradients are different in sign, i.e., they point to different sides of space and are of equal magnitude ($\underline{G}_1=-\underline{G}_2$) Therefore, just the directional dependency of the parameter of interest on the coat-thickness gradient is detected, with other conditions remaining constant.

In the simplest case, the coat thickness along the test track will have a minimum or a maximum, i.e., its course will have the form of a trough or peak. Since there is a constant change in the coat thickness, around the minimum/maximum, a continuous test track will traverse all coat thicknesses twice and with different gradients.

In particular, the coat thickness may change symmetrically along the test track, i.e., plotted as a function of the location, the coat thickness produces a mirror-symmetrical line. Specific symmetrical courses of this kind are, for example, bell-shaped or parabolic.

A sample coating of the aforementioned kind, with symmetry and a thickness maximum, may be produced, for example, by spraying along a straight line. As a result of the normal distribution of the spray mist with decreasing film thickness at the edges of the application, there is in fact automatically formation of a coat-thickness profile which extends in a bell shape transversely to the spray direction. Consequently, sample coatings of this kind can be produced using conventional methods and automatic equipment.

The test track may have a very general course. The expression "test track" refers quite generally to the temporally ordered sequence of the measurement sites. The test track corresponds to the path traveled by the measuring instruments over the sample coating, although only those sites at which measurements take place are ultimately relevant. For reasons of simplicity and mechanical operability of the measuring instruments, the test track will generally extend without reversals, and in the simplest case will be linear.

Using the method of the invention it is possible to measure, inter alia, coat thickness, evenness, shade, haze, and/or gloss of the sample coating. For all measurements, it is particularly preferred to record the coat thickness as well, in order to determine the dependency of these measurements on the coat thickness. Furthermore, it is possible in that case to monitor the presence of comparable coat thicknesses and to monitor the coat-thickness gradients in relation to the measurements. If, however, the coat-thickness course of the sample coating is sufficiently constant and reproducible, it may be possible to refrain from such subsequent measurement and to derive or estimate the coat thickness indirectly from the site of the measurement.

In the text below, the invention is illustrated by way of example with reference to the figures.

Figure 1:
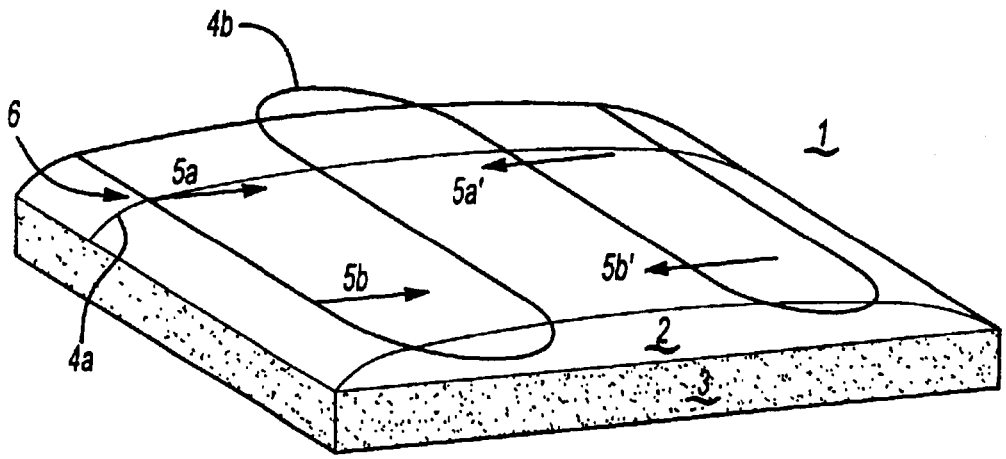
FIG. 1 shows a perspective view of the measurement of the invention.

FIG. 1 shows, in a perspective view, the principle of the measurement of the invention on a sample coating 1. The sample coating consists of a substrate 3, e.g., a metal panel, and of a coating film 2 applied thereon. The coat thickness of the coating film 2 shown has a curving, symmetrical course with c maximum in the center. The substrate 3 will generally be planar, as shown, although in principle it could also have an arbitrarily curved surface. In the case of a planar substrate, however, the conditions are more simple, since the film surface corresponds directly to the course of the coat thickness and therefore the inclination of this surface and the coat-thickness gradient are parameters which correspond to one another.

If the substrate base were to change in a nonplanar manner, then the coat thickness and its gradient would not be represented solely by the film surface. A limiting case in this context would be a planar film surface over a nonplanar substrate. In that case there would be no surface inclination and hence only the isolated influence of the coat-thickness gradient.

Also shown are test tracks 4a and 4b, of which one—4a—extends in the x-direction, the other—4b—in the y-direction. Drawn in on the tracks are exemplary gradient vectors 5a, 5a' and 5b, 5b', which should all be situated at the same coat thicknesses $SD_0$. The gradients lie parallel to the plane of the substrate 3 and point in the direction of maximum increase in coat thickness. If the measurement is performed along a test track 4a, then measurement takes place first at the coat thickness $SD_0$ with a positive gradient 5a and subsequently at the same coat thickness $SD_0$ with a negative gradient 5a'.

Similar comments apply to the test track 4b, which is traversed in parallel sections. In addition to the tracks 4a, 4b depicted by way of example, numerous other kinds of test tracks are also possible.

The vectorial gradients $\underline{G}$ are defined mathematically by way of the derivation of the function $f(\underline{r})$, which in a coordinate system with (two-dimensional) site vector $\underline{r}$ describes the surface of the coating film 2, i.e.:

$$\underline{G}:=\mathrm{grad}(f)=\nabla f=df/d\underline{r}$$

The arrow 6 symbolizes the viewing direction of a measuring instrument, e.g., of a calorimeter. While it is possible in principle for the viewing direction to change along the test track, it is an advantage of the method of the invention that it may remain constant (i.e., is shifted only in parallel). This considerably simplifies the guidance of the measuring instruments. With this setup, the directional variations required for the measurement are obtained by means of the specific course of the coat thickness and of the test track, in accordance with the invention.

Figure 2:
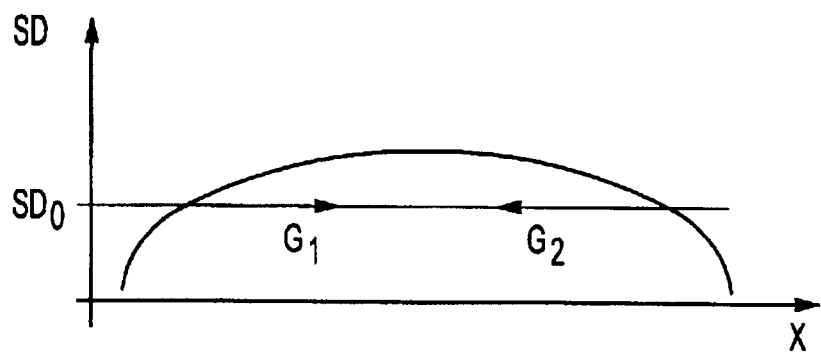
FIG. 2 shows the coat thickness as a function of the measurement path.

FIG. 2 shows, diagrammatically, the plot of the coat thickness SD(x) of the coating film 2 from FIG. 1 over the path section x traveled on the test track 4a. The curved course can be seen, with the gradients $\underline{G}_1$ and $\underline{G}_2$ at the coat thickness $SD_0$. Owing to the linear course of the test track 4a transverse to the curve of the coating, the gradients in this case correspond to the derivation dSD/dx.

Figure 3:
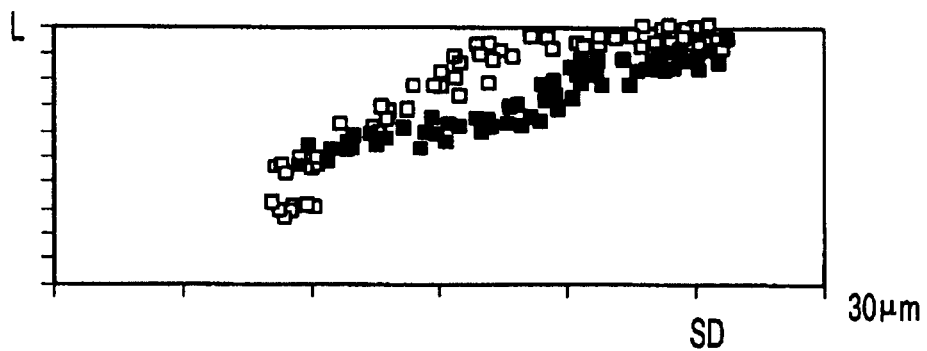
FIG. 3 shows measured brightness values as a function of the coat thickness.

FIG. 3, finally, shows a real measurement of the brightness L* (CIELAB system) in accordance with the principle illustrated in FIG. 1 (track 4a). In the diagram, the brightness is plotted as a function of the coat thickness SD. The corresponding coat thicknesses may be measured either at: the same time as the brightness or else calculated from a known correlation between coat thickness SD and path section x traveled on the test track (cf. FIG. 2).

The measurements plotted are shown with different symbols for the rising and the falling sections of the test track. Finally, for each coat thickness $SD_0$ between about 10 and 25 μm, there are two measurements which can be seen in relation to two different gradients. From the plot it emerges that these measurements diverge in the manner of a hysteresis, i.e., the coating looks different from two viewing directions rotated by 180° (and under otherwise identical conditions). A difference of this kind, however, is not tolerable, something which can be discovered for the coating material in question directly on the basis of a measurement in accordance with the invention.

What is claimed is:

1. A method of determining direction-dependent properties of coatings comprising measuring at least one coating properties along a test track on a sample coating using at least one measuring instruments to give at least one measurement,
   wherein
   a) at least one of the at least one measurement is recorded in relation to direction,
   b) the sample coating has at least one coat thickness that occurs at two points and at at least two different coat-thickness gradients along the test track, and
   c) the measuring is done at least at these two points.

2. The method of claim 1, wherein the at least two coat-thickness gradients are different in sign.

3. The method of claim 1, wherein the at least one coat thickness has a minimum or a maximum along the test track.

4. The method of claim 1, wherein the coat thickness changes symmetrically along the test track.

5. The method of claim 4, wherein the coat thickness changes symmetrically along ie test track in a bell-shape.

6. The method of claim 4, wherein the coat thickness changes symmetrically along the test track in a parabolic shape.

7. The method of clam 1, which is used to measure coat thickness, evenness, shade, haze, and/or gloss of the sample coating.

8. The method of claim 1, wherein the sample coating is produced by sprang along a straight line.

9. The method of claim 1, wherein the test track extends without reversals.

10. The method of claim 9, wherein the test track extends linearly.

11. The method of claim 1, wherein the measuring is done in one pass along the test track.

12. The method of claim 1, wherein the measurement recorded in relation to direction is based on a relative angle between a measuring direction and a second direction.

13. The method of claim 12, wherein the second direction is related to the surface of the sample coating.

14. The method of claim 12, wherein the second direction is relative to the coat thickness gradient.

* * * * *